US009139525B2

(12) United States Patent
Wikström (10) Patent No.: US 9,139,525 B2
(45) Date of Patent: Sep. 22, 2015

(54) N-OXIDE AND/OR DI-N-OXIDE DERIVATIVES OF DOPAMINE RECEPTOR STABILIZERS/MODULATORS DISPLAYING IMPROVED CARDIOVASCULAR SIDE-EFFECTS PROFILES

(75) Inventor: Håkan V. Wikström, Hamburgsund (SE)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 497 days.

(21) Appl. No.: 12/595,472

(22) PCT Filed: Apr. 11, 2008

(86) PCT No.: PCT/SE2008/050414
§ 371 (c)(1),
(2), (4) Date: Dec. 17, 2009

(87) PCT Pub. No.: WO2008/127188
PCT Pub. Date: Oct. 23, 2008

(65) Prior Publication Data
US 2010/0105736 A1    Apr. 29, 2010

(30) Foreign Application Priority Data

Apr. 12, 2007    (SE) ........................................ 0700893

(51) Int. Cl.
*C07D 211/94*    (2006.01)
*A61K 31/445*    (2006.01)

(52) U.S. Cl.
CPC .................................... *C07D 211/94* (2013.01)

(58) Field of Classification Search
CPC ............................ C07D 211/94; A61K 31/445
USPC .......... 514/317, 326, 331, 327; 546/212, 214, 546/230, 232, 233, 236, 237, 217
See application file for complete search history.

(56) References Cited

U.S. PATENT DOCUMENTS

| | | | | |
|---|---|---|---|---|
| 5,462,947 | A * | 10/1995 | Svensson et al. | ............. 514/317 |
| 6,121,259 | A | 9/2000 | Yelle | |
| 6,903,120 | B2 * | 6/2005 | Sonesson et al. | ............. 514/331 |
| 6,924,374 | B2 | 8/2005 | Sonesson et al. | |
| 7,417,043 | B2 | 8/2008 | Sonesson et al. | |
| 7,923,459 | B2 | 4/2011 | Gauthier et al. | |
| 2007/0149542 | A1 | 6/2007 | Sonesson et al. | |
| 2008/0234321 | A1 | 9/2008 | Sonesson | |
| 2013/0150406 | A1 | 6/2013 | Zimmermann et al. | |
| 2013/0197031 | A1 | 8/2013 | Sonesson et al. | |
| 2013/0267552 | A1 | 10/2013 | Waters et al. | |
| 2014/0088140 | A1 | 3/2014 | Hayden et al. | |
| 2014/0088145 | A1 | 3/2014 | Hayden et al. | |

FOREIGN PATENT DOCUMENTS

| | | | |
|---|---|---|---|
| WO | WO 92/18475 | A2 | 10/1992 |
| WO | WO 01/46145 | A1 | 6/2001 |
| WO | WO 01/46146 | A1 | 6/2001 |
| WO | WO 03/064393 | A1 | 8/2003 |
| WO | WO 2005/121087 | A1 | 12/2005 |
| WO | WO 2007/023141 | A1 | 3/2007 |
| WO | WO 2007/042295 | A1 | 4/2007 |
| WO | WO 2007/128694 | A1 | 11/2007 |
| WO | WO2011/107583 | * | 9/2011 |
| WO | WO2011/107593 | * | 9/2011 |
| WO | WO 2013/034622 | | 3/2013 |

OTHER PUBLICATIONS

Augst et al. "Prodrugs to reduce pre . . . " p. 340-355 (2007).*
Bickel et al. "Pharmacology . . . " Pharm Rev. v.21(4) p. 325-355 (1969).*
Dowald "side rection . . . " p. ix (2005).*
Kalgutkar et al. "identification of . . . " Drug Meta.and Disposition v.32(9) p. 943-952 (2004).*
Katritzky et al. "conformational . . . " CA75:48309 (1971).*
Rajsner et al. "Neurotropic . . . " CA90:22967 (1979).*
Sanner "Selective dopamine . . . " Exp. Opino Ther. Patents vol. 8(4) p. 383-393 (1998).*
Aungst et al. "Prodrugs to reduce pre . . . " p. 340-355 (2007).*
Bickel et al. "Pharmacology . . . " Pharm Rev. v.21(4) p. 325-355 (1969)n.*
Loperamide prodrug Wikipedia p. 1 (2012).*
Testa "Prodrugs . . . " Curr. Opion. Chme. Biol.v. 13 p. 338-344 (2009).*
Sonesson et al., "Substituted (S)-Phenylpiperidines and Rigid Congeners as Preferential Dopamine Autoreceptor Antagonists: Synthesis and Structure-Activity Relationships," J. Med. Chem., 1994, vol. 37, pp. 2735-2752.*
"Examination guidelines updates . . . " Fed. Reg. p. 1-34, Sep. 2010.*
"prodrug" definition, medical dictionary p. 1 (2004).*
Calligaro et al., "The Synthesis and Biological Activity of Some Known and Putative Metabolites of the Atypical Antipsychotic Agent Olanzapine (LY170053)," Bioorganic & Medicinal Chemistry Letters, vol. 7, No. 1, pp. 25-30, 1997.
Grundt et al., "Heterocyclic Analogues of N-(4-(4-(2,3-Dichlorophenyl)piperazin-1-yl)butyl)arylcarboxamides with Functionalized Linking Chains as Novel Dopamine D3 Receptor Ligands: Potential Substance Abuse Therapeutic Agents," J. Med. Chem., 2007, vol. 50, pp. 4135-4146.
U.S. Appl. No. 14/040,579, filed Sep. 27, 2013, Hayden and Fitzer-Attas.
U.S. Appl. No. 14/040,586, filed Sep. 27, 2013, Hayden and Bar-Zohar.
Jul. 30, 2003 Office Action in connection with U.S. Appl. No. 10/168,173.
Jan. 30, 2004 Response to Jul. 30, 2003 Office Action in connection with U.S. Appl. No. 10/168,173.
Apr. 23, 2004 Office Action in connection with U.S. Appl. No. 10/168,173.
Oct. 25, 2004 Response to Apr. 23, 2004 Office Action in connection with U.S. Appl. No. 10/168,173.
International Search Report and the Written Opinion of the International Searching Authority, or the Declaration, including and International Search Report and Written Opinion of the International Searching Authority, completed Mar. 21, 2002, in connection with PCT International Application No. PCT/SE00/02674, filed Dec. 22, 2000 Office Action issued Apr. 28, 2003 in connection with European Patent Application No. 00 989162.3-2101.
Jul. 26, 2005 Office Action in connection with U.S. Appl. No. 11/016,967.
Aug. 23, 2005 Response to Jul. 26, 2005 Office Action in connection with U.S. Appl. No. 11/016,967.

Dec. 7, 2005 Office Action in connection with U.S. Appl. No. 11/016,967.
Apr. 7, 2006 Response to Dec. 7, 2005 Office Action in connection with U.S. Appl. No. 11/016,967.
Jun. 28, 2006 Office Action in connection with U.S. Appl. No. 11/016,967.
Sep. 27, 2006 Response to Jun. 28, 2006 Office Action in connection with U.S. Appl. No. 11/016,96.
Aug. 9, 2007 Office Action in connection with U.S. Appl. No. 11/016,967.
Jan. 9, 2008 Response to Aug. 9, 2007 Office Action in connection with U.S. Appl. No. 11/016,967.
Sep. 26, 2008 Office Action in connection with U.S. Appl. No. 11/733,512.
Dec. 23, 2008 Response to Sep. 26, 2008 Office Action in connection with U.S. Appl. No. 11/733,512.
Mar. 12, 2009 Office Action in connection with U.S. Appl. No. 11/733,512.
Sep. 6, 2009 Response to Mar. 12, 2009 Office Action in connection with U.S. Appl. No. 11/733,512.
Aug. 24, 2009 Office Action in connection with U.S. Appl. No. 11/733,512.
Feb. 22, 2007 International Preliminary Report on Patentability and Written Opinion of the International Search Authority for PCT International Application No. PCT/EP05/011020 (WO 2006/040155) published Apr. 20, 2006 (Gauthier et al.).
International Preliminary Report on Patentability and Written Opinion of the International Search Authority for PCT International Application No. PCT/EP2011/064954, filed Aug. 31, 2011 (WO 2012/028635) (Sonesson).
Notification of Transmittal of the International Search Report and the Written Opinion of the International Searching Authority, or the Declaration, including an International Search Report and Written Opinion of the International Searching Authority, mailed Feb. 22, 2013 in connection with PCT International Application No. PCT/US2012/68582 filed Dec. 7, 2012.
Notification of Transmittal of the International Search Report and the Written Opinion of the International Searching Authority, or the Declaration, including an International Search Report and Written Opinion of the International Searching Authority, mailed Jul. 22, 2013 in connection with PCT International Application No. PCT/US2013/035124 filed Apr. 3, 2013.
Oct. 4, 2012 International Search report for PCT International Publication No. WO/2013/034622 (PCT/EP12/067371) published Mar. 14, 2013 (Sonesson).
Oct. 13, 2009 International Preliminary Report on Patentability and Written Opinion of the International Search Authority for PCT International Application No. PCT/SE2008/050414 (WO 2008/127188 A1), published Oct. 23, 2008 (Wikström).
Oct. 22, 2012 Office Action issued by the European Patent Office in connection with European Patent Application No. 08 741 904.0.
Apr. 30, 2013 Response to Oct. 22, 2012 Office Action filed in connection European Patent Application No. 08 741 904.0.
Jun. 22, 2012 Office Action issued by the Australian Patent Office in connection with Australian Patent Application No. 2008239841.
Jun. 21, 2013 Response to Jun. 22, 2012 Office Action filed in connection with Australian Patent Application No. 2008239841.
Jul. 31, 2012 Office Action issued by the Israeli Patent Office in connection with Israeli Patent Application No. 201401 (translation).
May 24, 2013 Office Action issued by the Japanese Patent Office in connection with Japanese Patent Application No. 2010-502976 (with English Language translation).
Aug. 23, 2013 Response to May 24, 2013 Office Action filed in connection with Japanese Patent Application No. 2010-502976 (with English draft sent to Japanese associates for filing).
Feb. 21, 2012 First Office Action issued by the Mexican Patent Office in connection with Mexican Patent Application No. MX/a/2009/011020 (Translation).
Apr. 18, 2012 Response to Feb. 21, 2012 First Office Action filed in connection with Mexican Patent Application No. MX/a/2009/011020 (with Google Translate™ translation of main text to English).

Sep. 25, 2012 Response to Aug. 22, 2012 Second Office Action filed in connection with Mexican Patent Application No. MX/a/2009/011020 (with Google Translate™ translation of main text to English).
Feb. 8, 2013 Third Office Action issued by the Mexican Patent Office in connection with Mexican Patent Application No. MX/a/2009/011020 (with Google Translate™ translation of main text to English.
Apr. 29, 2013 Response to Feb. 8, 2013 Third Office Action filed in connection with Mexican Patent Application No. MX/a/2009/011020 (with English draft sent to Mexican associates for filing).
Jul. 26, 2011 First Office Action issued by the Chinese Patent Office in connection with Chinese Patent Application No. 200880017598.8 (with English Language translation).
Dec. 9, 2011 Response to Jul. 26, 2011 First Office Action filed in connection with Chinese Patent Application No. 200880017598.8 (with English Language translation of claims).
Feb. 22, 2012 Second Office Action issued by the Chinese Patent Office in connection with Chinese Patent Application No. 200880017598.8 (with English Language translation).
May 7, 2012 Response to Feb. 22, 2012 Second Office Action filed in connection with Chinese Patent Application No. 200880017598.8 (with English Language translation of claims).
Oct. 8, 2010 Office Action issued by the New Zealand Patent Office in connection with New Zealand Patent Application No. 580586.
Oct. 7, 2011 Response to Oct. 8, 2010 Office Action filed in connection with New Zealand Patent Application No. 580586.
Feb. 15, 2012 Office Action issued by the Russian Patent Office in connection with Russian Patent Application No. 2009141300/04(058696) (with English Language translation).
Jul. 13, 2012 Response to Feb. 15, 2012 Office Action filed in connection with Russian Patent Application No. 2009141300/04(058696) (with English Language translation of claims and Google Translate™ translation of main text of Office Action to English).
U.S. Appl. No. 14/342,253, Clas Sonesson et al.
U.S. Appl. No. 14/309,111, Merav Bassan et al.
Feb. 26, 2014 Office Action issued by the Canadian Patent Office in connection with Canadian Patent Application No. 2,683,719.
May 5, 2014 Response to Nov. 5, 2013 Final Office Action and Mar. 11, 2014 Advisory Action in connection with U.S. Appl. No. 13/708,816.
Mar. 11, 2014 Advisory Action issued in connection with U.S. Appl. No. 13/708,816.
Feb. 5, 2014 Response to Nov. 5, 2013 Final Office Action issued in connection with U.S. Appl. No. 13/708,816.
Jun. 18, 2014 Office Action in connection with U.S. Appl. No. 13/708,816.
Apr. 26, 2006 letter to European Patent Office from A. Carlsson Research AB, applicant of PCT International Application No. PCT/EP2005/011020.
Oct. 5, 2009 Response to Aug. 24, 2009 Office Action in connection with U.S. Appl. No. 11/733,512.
Nov. 17, 2009 Office Action in connection with U.S. Appl. No. 11/733,512.
Feb. 17, 2010 Response to Nov. 17, 2009 Office Action in connection with U.S. Appl. No. 11/733,512.
Declaration filed in connection with U.S. Appl. No. 11/733,512, (Aug. 13, 2010.
Aug. 18, 2010 Office Action in connection with U.S. Appl. No. 11/733,512.
Nov. 12, 2010 Response to Aug. 18, 2010 Office Action in connection with U.S. Appl. No. 11/733,512.
May 17, 2013 Office Action in connection with U.S. Appl. No. 13/708,816.
Aug. 16, 2013 Amendment in response to May 17, 2013 Office Action in connection with U.S. Appl. No. 13/708,816.
Nov. 5, 2013 Final Office Action issued in connection with U.S. Appl. No. 13/708,816.

\* cited by examiner

*Primary Examiner* — Celia Chang

(74) Attorney, Agent, or Firm — John P. White; Gary J. Gershik; Cooper & Dunham LLP (57) ABSTRACT

A compound having the general formula wherein A is selected from the group consisting of to the formation of a compound of the general formula (1)

(1)

and a compound of the general formula (2)

(2)

respectively, and pharmaceutically acceptable salts thereof, wherein $R^1$ is a member selected from the group consisting of $CF_3$, $OSO_2CF_3$, $OSO_2CH_3$, $SOR^4$, $SO_2R^4$, $COR^4$, $CN$, $OR^4$, $NO_2$, $CONHR^4$, 3-thiophene, 2-thiophene, 3-furane, 2-furane, F, Cl, Br and I, wherein $R^4$ is as defined below;

$R^2$ is a member selected from the group consisting of H, F, Cl, Br, I, CN, $CF_3$, $CH_3$, $OCH_3$, OH, $NH_2$, $SO_mCF_3$, $O(CH_2)_m CF_3$, $SO_2N(R^4)_2$, $CH=NOR^4$, $COCOOR^4$, $COCOON(R^4)_2$, $(C_1-C_8)$alkyl, $(C_3-C_8)$cykloalkyl, $CH_2OR^4$, $CH_2(R^4)_2$, $NR^4SO_2CF_3$, $NO_2$, at phenyl at positions 2, 4, 5 or 6, wherein x and $R^4$ are as defined below;

$R^3$ is a member selected from the group consisting of hydrogen, $CF_3$, $CH_2CF_3$, $(C_1-C_8)$alkyl, $(C_3-C_8)$cykloalkyl, $(C_4-C_9)$cycloalkylmethyl, $(C_2-C_8)$alkenyl, $(C_2-C_8)$alkynyl, 3,3,3-tri-fluoropropyl, 4,4,4-trifluorobutyl, $CH_2SCH_3$, $CH_2CH_2OCH_3$, $CH_2CH_2CH_2F$, $CH_2CF_3$, phenylethyl, 2-thipheneethyl and 3-thipheneethyl;

$R^4$ is a member selected from the group consisting of hydrogen, $CF_3$, $CH_2CF_3$, $(C_1-C_8)$alkyl, $(C_3-C_8)$cycloalkyl, $(C_4-C_9)$cycloalkylmethyl, $(C_2-C_8)$alkenyl, $(C_2-C_8)$alkynyl, 3,3,3-trifluoropropyl, 4,4,4-trifluorobutyl, 2-tetrahydrofurane and 3-tetrahydrofurane;

X is selected from the group consisting of N and $sp^3$-hybridized C;

Y is selected from the group consisting of O and, when $R_3$ represents H, OH;

Z is selected from the group consisting of H and OH when X is $sp^3$-hybridized C or Z represents O or an electronic lone-pair when X is N;

the dashed line represents a bond when X is $sp^2$-hybridized C or is absent when X is N;

m is an integer 1 or 2;

n is an integer 1-3;

provided that when n in Formula 1 is 2, $R^1$ is $SO_2CH_3$ and $R^2$ is H $R^3$ does not represent n-propyl.

The invention also relates to a pharmaceutical preparation containing said compound, the use of said compound for the manufacture of a pharmaceutical composition and a method for the treatment of a disorder in the central nervous system of a patient using said compound.

2 Claims, 1 Drawing Sheet

N-OXIDE AND/OR DI-N-OXIDE DERIVATIVES OF DOPAMINE RECEPTOR STABILIZERS/MODULATORS DISPLAYING IMPROVED CARDIOVASCULAR SIDE-EFFECTS PROFILES

BACKGROUND OF THE INVENTION

1. Field of Invention

This invention relates to N-oxide and/or di-N-oxide derivatives of "dopamine receptor stabilizers/modulators" (examples of stabilizers are OSU6162 and ACR16), having improved therapeutic potential, improved oral bioavailability, improved side-effects profile, in particular with respect to decreasing the risk of eliciting a prolongation of the QT interval and thereby also decreasing the risk of eliciting Torsades de Pointes, and a longer duration of action, as well as pharmaceutical compositions comprising these compounds and suitable pharmaceutical carriers, methods of treating neurological and/or psychiatric diseases in a mammal using the drugs, and methods for preparing the drugs.

2. Background Art about N-Oxides/Di-N-Oxides

The N-oxides of certain morphinan derivatives are known in the prior art, e.g., Tiffany, U.S. Pat. No. 2,813,097, discloses 3-hydroxy-N-methyl-morphinan N-oxide and its utility as an analgesic. Tiffany, U.S. Pat. No. 2,813,098, discloses 3-methoxy-N-methylmorphinan N-oxide and its utility as an antitussive agent. Although it is stated that these N-oxides have a higher therapeutic index than the corresponding tertiary amines, there is no suggestion that the N-oxide of 3-hydroxy-N-methyl morphinan might have improved oral bioavailability relative to the parent compound.

Bartels-Keith, U.S. Pat. No. 3,299,072, discloses thebaine derivatives. These compounds have analgesic and/or narcotic antagonist activity. The reference claims the tertiary amines, the N-oxides, and various salts of the stated formula without distinguishing the N-oxides in any way. There is no mention of route of administration.

N-oxide derivatives of other non-morphinan analgesics have been reported. W. Graf, Swiss Pat. No. 481, 124.

K. Orzechowska, Arch. Immunol. Ther. Exp. 15(2), 290 (1967), and B. Bobranski and J. Pomorski, Arch. Immunol. Ther. Exp. 14(1), 121 (1966) report the preparation of the N-oxides of certain 1-alkyl-4-phenyl-4-acyloxy piperidine compounds. The N-oxide of 1-methyl-4-phenyl-4-propionoxypiperidine HCl exhibited analgesic activity equal to that of dolantin HCl, but of longer duration. Toxicity was also less.

The N-oxides of morphine and simple morphine derivatives such as codeine, hydromorphone (dihydromorphinone), and hydrocodone (dihydro codeinone), are well known, having been reported by, among others: M. Polonovski et al, Bull. Acad. Med. 103, 174 (1930); N. H. Chang et al, J. Org. Chem. 15, 634 (1950); B. Kelentei et al, Arzneimittel-Forsch. 7, 594 (1957); K. Takagi et al, Yakugaku Zasshi 83, 381 (1963) (Chem. Abs. 59: 9224b); L. Lafon, U.S. Pat. No. 3,131,185; M. R. Fennessy, Brit. J. Pharmacol. 34, 337 (1968); M. R. Fennessy, Eur. J. Pharmacol. 8, 261 (1969); and M. R. Fennessy, J. Pharm. Pharmacol. 21, 668 (1969). Morphine N-oxide is variously reported to be either less active or inactive as an analgesic but an effective antitussive, as well as having somewhat lower toxicity than morphine. There is no indication, however, that these N-oxides were ever administered orally, nor any suggestion that they might exhibit improved oral bioavailability.

Woods, Brit. Pat. No. 1,217,296, discloses the use of a combination of morphine N-oxide and amiphenazole as an analgesic composition. The combination is said to enhance the analgesic activity of morphine N-oxide while reducing the side-effects of both compounds.

Oxidative metabolism to an N-oxide which is excreted is among the many metabolic pathways which have been identified in mammals administered various tertiary amines. J. D. Phillipson et al, Eur. J. Drug Metab. Pharmacokinetics 3, 119 (1978), report that morphine and codeine are converted in part to the corresponding N-oxides by a guinea pig liver microsomal preparation, and also that these two drugs are partially metabolized to the N-oxides when administered to rats. T. Ishida et al, Drug Metab. Dispos. 7, 162 (1979), and T. Ishida et al, J. Pharmacobio-Dyn. 5, 521 (1982), report that oxycodone N-oxide is one of a number of identifiable metabolites found in the urine of rabbits administered oxycodone subcutaneously. While other metabolites were found in both free and conjugated forms, oxycodone-N-oxide was found only in the free, unconjugated form. The analgesic activity of oxycodone is believed to be due to the unchanged drug rather than the metabolites. S. Y. Yeh et al, J. Pharm. Sci. 68, 133 (1979), also report isolating morphine N-oxide from the urine of guinea pigs administered morphine sulfate.

Certain tertiary amine N-oxides are partially metabolized by reduction to the tertiary amine upon administration to test animals. R. L. H. Heimans et al, J. Pharm. Pharmacol. 23, 831 (1971) report that morphine N-oxide is partially reduced to morphine after administration to rats. T. Chyczewski, Pol. J. Pharmacol. Pharm. 25, 373 (1973), reports that the N-oxide of 1-methyl-4-phenyl-4-piperidinol propionate is partially reduced to the tertiary amine following administration to rabbits, mice, and rats. P. Jenner et al, Xenobiotica 3 (6), 341 (1973), report that nicotine-1'-N-oxide is partially reduced to nicotine in man after oral administration, but not after intravenous administration. Oral administration of nicotine-1'-N-oxide substantially avoids the first-pass phenomenon seen with oral nicotine. The reduction to nicotine which occurs in the lower gastrointestinal tract is believed to be by GI flora.

It is well established that N-oxidation of the aliphatic tertiary amine group(s) in the N-10 side chain of Phenothiazine antipsychotics agents is a major route of metabolism of these drugs in humans (Yeung, P. K., et al., J Pharm Sci, 1987. 76(10): p. 803-8; Marder, S. R., et al., Psychopharmacol Bull, 1989. 25(3): p. 479-82; Aravagiri, M., et al., Ther Drug Monit, 1990. 12(3): p. 268-76; Marder, S. R., et al., Psychopharmacol Bull, 1990. 26(2): p. 256-9; Marder, S. R., et al., Br J Psychiatry, 1991. 158: p. 658-65; Hubbard, J. W., et al., Br J Psychiatry Suppl, 1993(22): p. 19-24; Javorski, T. J. and M. S. Sardessai, Journal of Pharmaceutical Sciences, 1993. 82(3): p. 330-333; Midha, K. K., et al., Ther Drug Monit, 1993. 15(3): p. 179-89; Yeung, P. K., et al., Eur J Clin Pharmacol, 1993. 45(6): p. 563-9; Aravagiri, M., et al., Ther Drug Monit, 1994. 16(1): p. 21-9).

High plasma levels of N-oxide metabolites have been seen in humans for chlorpromazine, fluphena-zine, and trifluoroperazine. However, the true contribution of these metabolites to the clinical response has been investigated only in the case of fluphenazine. Fluphenazine N4-oxide was more strongly associated with side-effects than was the parent drug. Chlorpromazine N-oxide was, on the contrary, devoid of antidopaminergic effects. However, chlorpromazine N-oxide is converted to chlorpromazine in humans, and its metabolic profile is very similar to that of the parent drug. It is known that both clozapine N-oxide (Chang, W., et al., Prog Neuropsychopharmacol Biol Psychiatry, 1998. 22(5): p. 723-739) and olanzapine N-oxide (U.S. Pat. No. 6,352,984 B1) are metabolites of clozapine and olanzapine, respectively. It is also known that their corresponding N-oxides are prodrugs, generating clozapine and olanzapine, respectively.

The oral administration of many drugs will usually elicit a substantially lesser response as compared to an equal dose administered parenterally. This reduction in potency most commonly results from an extensive metabolism of the drug during its transit from the gastrointestinal tract to the general circulation. For example, the intestinal mucosa and the liver, through which an orally administered drug passes before it enters the systemic circulation, are very active enzymatically and can thus metabolize the drug in many ways.

When an orally administered drug is rapidly metabolized to an inactive or significantly less active form by the gastrointestinal system or liver prior to entering the general circulation, its bioavailability is low. In certain instances, this problem can be circumvented by administering the drug by another route. Examples of such alternative routes include nasal (propranolol), sublingual (nitroglycerin) and inhalation (cromolyn sodium). Drugs administered by these routes avoid hepatic and gut-wall metabolism on their way to the systemic circulation.

In some instances, the presystemic metabolism of certain orally administered drugs can be overcome by derivatization of the functional group in the molecule that is susceptible to gastrointestinal or hepatic metabolism. This modification protects the group from metabolic attack during the absorption process or first pass through the liver. However, the masking group must ultimately be removed to enable the drug to exert its maximum effect, and since the masking group is released into the body, it must be relatively non-toxic. This conversion may take place in blood or tissue. These types of masked drugs are usually referred to as prodrugs.

Background Art about Dopaminergic Regulation/Modulation

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous (e.g. regulation of appetite, body temperature, sleep) functions. Thus, modulation of dopaminergic function may be beneficial in the treatment of a wide range of disorders affecting brain functions. In fact, both neurologic and psychiatric disorders are treated with medications based on interactions with dopamine systems and dopamine receptors in the brain.

Drugs that act, directly or indirectly, at central dopamine receptors are commonly used in the treatment of neurological and psychiatric disorders, e.g. Parkinson's disease and schizophrenia. Currently available dopaminergic pharmaceuticals have severe side effects, such as extrapyramidal side effects and tardive dyskinesia in dopaminergic antagonists used as antipsychotic agents, and dyskinesias and psychoses in dopaminergic agonists used as anti-Parkinson's agents. Therapeutic effects are unsatisfactory in many respects. To improve efficacy and reduce side-effects of dopaminergic pharmaceuticals, novel dopamine receptor ligands with selectivity at specific dopamine receptor subtypes or regional selectivity are sought for. In this context, also partial dopamine receptor agonists, i.e. dopamine receptor ligands with some, but not full, intrinsic activity at dopamine receptors, are being developed to achieve an optimal degree of stimulation at dopamine receptors, avoiding excessive dopamine receptor blockade or excessive dopamine stimulation.

Compounds belonging to the class of substituted 3-(phenyl-N-alkyl)piperidines, 4-(phenyl-N-alkyl)piperazines and substituted 4-(phenyl-N-alkyl)piperidines have been previously reported (e.g. OSU6162 and ACR16). Among these compounds, some are inactive in the CNS, some display serotonergic or mixed serotonergic/dopaminergic pharmacological profiles, while some are full or partial dopamine receptor antagonists or agonists with high affinity for dopamine receptors.

A number of 4-phenylpiperazines and 4-phenyl-piperidine derivatives are known and described, for example Costall et al. European J. Pharm. 31, 94, (1975), and Mewshaw et al. Bioorg. Med. Chem. Lett., 8, 295, (1998). The reported compounds are substituted 4-phenyl-piperazines, most of them being 2-, 3- or 4-OH phenyl substituted and displaying DA autoreceptor agonist properties.

Fuller R. W. et al., J. Pharmacol. Exp. Therapeut. 218, 636, (1981) disclose substituted piperazines (e.g. 1-(m-trifluoromethylphenyl)pi-perazine) which reportedly act as serotonin agonists and inhibit serotonin uptake. Fuller R. W. et al Res., Commun. Chem. Pathol. Pharmacol. 17, 551, (1977) disclose the comparative effects on the 3,4-dihydroxyphenylacetic acid and Res. Commun. Chem. Pathol. Pharmacol. 29, 201, (1980) disclose the comparative effects on the 5-hydroxyindole acetic acid concentration in rat brain by 1-(p-chlorophenol)-piperazine.

Boissier J. et al., Chem. Abstr. 61:10691c, disclose disubstituted piperazines. The compounds are reportedly adrenolytics, antihypertensives, potentiators of barbi-turates, and depressants of the central nervous system. In addition, Akasaka et al. (EP 0675118) disclose bifenylderivatives of piperazines, which exhibits dopamine D2 receptor antagonism and/or 5-HT2 receptor antagonism.

A number of different substituted piperazines have been published as ligands at 5-HT1A receptors, for example Glennon R. A. et al. J. Med. Chem., 31, 1968, (1988) and van Steen B. J., J. Med. Chem., 36, 2751, (1993), Dukat M.-L., J. Med. Chem., 39, 4017, (1996). Glennon R. A. discloses, in international patent applications WO 93/00313 and WO 91/09594, various amines, among them substituted piperazines, as sigma receptor ligands. Clinical studies investigating the properties of sigma receptor ligands in schizophrenic patients have not generated evidence of antipsychotic activity, or activity in any other CNS disorder. Two of the most extensively studied selective sigma receptor antagonists, BW234U (rimcazole) and BMY14802, have both failed in clinical studies in schizophrenic patients (Borison et al, 1991, Psychopharmacol Bull 27(2): 103-106; Gewirtz et al, 1994, Neuropsychopharmacology 10:37-40).

The recent patent application entitled "Noncardiotoxic pharmaceutical compounds." by Donald L. Barbeau (US) (Pub. No. 20060035863/Pub. Date: 16 Feb. 2006 Ser. No. 11,199,866/Filed Date: 9 Aug. 2005, U.S. class: 514/89; 546/21, International class: A61K 31/675; C07F 9/59, provisional application No. 60,600,699, filed on 11 Aug. 2004, provisional application No. 60,673,545, filed on 21 Apr. 2005), relates to novel noncardiotoxic compounds and pharmaceutical compositions useful in the treatment of a variety of dis-orders including the treatment of depression, allergies, psychoses, cancer and gastrointestinal disorders. In particular, that invention describes pharmaceutical compositions that mitigate life-threatening arrhythmias such as torsade de pointes based on the fact that the high plasma levels of the cardiotoxic hydroxylated metabolites are avoided by the use of a noncardiotoxic prodrug, which was designed to be noncardiotoxic in its own right. By circumventing the first pass secondary metabolism, those hydroxylated metabolites will only be formed in a much smaller concentration than would be the case when administering the active principle itself.

Even though N-oxides are mentioned in the patent of Barbeau (see above), the present invention is directed to N-oxides of a certain class of dopamine receptor stabilizers related to

OSU6162 and ACR16. It was surprisingly found that some of the claimed compounds, beside their ability to stabilize DA receptors via a reductive bioactivation pathway, also have an effect of their own on the DA receptor. Also surprisingly, it was found that these prodrugs have a pharmacokinetic profile which decrease the risk of serious cardiovascular side-effects (e.g. QTc and Torsades de Pointes).

DISCLOSURE OF THE INVENTION

The present invention relates to N-oxide and/or di-N-oxide derivatives of dopamine receptor stabilizers/modulators having the general formula wherein A is selected from the group consisting of to the formation of a compound of the general formula (1)

and a compound of the general formula (2)

respectively, and pharmaceutically acceptable salts thereof, wherein
$R^1$ is a member selected from the group consisting of $CF_3$, $OSO_2CF_3$, $OSO_2CH_3$, $SO_2R^4$, $SO_2R^4$, $COR^4$, $CN$, $OR^4$, $NO_2$, $CONHR^4$, 3-thiophene, 2-thiophene, 3-furane, 2-furane, F, Cl, Br and I, wherein $R^4$ is as defined below;
$R^2$ is a member selected from the group consisting of H, F, Cl, Br, I, CN, $CF_3$, $CH_3$, $OCH_3$/OH, $NH_2$, $SO_mCF_3$, $O(CH_2)_m$ $CF_3$, $SO_2N(R^4)_2$, $CH=NOR^4$, $COCOOR^4$, $COCOON(R^4)_2$, $(C_1$-$C_8)$alkyl, $(C_3$-$C_8)$cykloalkyl, $CH_2OR^4$, $CH_2(R^4)_2$, $NR^4SO_2CF_3$, $NO_2$, at phenyl at positions 2, 4, 5 or 6, wherein x and $R^4$ are as defined below;
$R^3$ is a member selected from the group consisting of hydrogen, $CF_3$, $CH_2CF_3$, $(C_1$-$C_8)$alkyl, $(C_3$-$C_8)$cykloalkyl, $(C_4$-$C_9)$ cycloalkylmethyl, $(C_2$-$C_8)$alkenyl, $(C_2$-$C_8)$alkynyl, 3,3,3-trifluoropropyl, 4,4,4-trifluorobutyl, $CH_2SCH_3$, $CH_2CH_2OCH_3$, $CH_2CH_2CH_2F$, $CH_2CF_3$, phenylethyl, 2-thiopheneethyl and 3-thiopheneethyl;
$R^4$ is a member selected from the group consisting of $CF_3$, $CH_2CF_3$, $(C_1$-$C_8)$alkyl, $(C_3$-$C_8)$cycloalkyl, $(C_4$-$C_9)$cycloalkylmethyl, $(C_2$-$C_8)$alkenyl, $(C_2$-$C_8)$alkynyl, 3,3,3-trifluoropropyl, 4,4,4-trifluorobutyl, 2-tetrahydrofurane and 3-tetrahydrofurane;
X is selected from the group consisting of N and $sp^3$-hybridized C;
Y is selected from the group consisting of O and, when $R_3$ represents H, OH;
Z is selected from the group consisting of H and OH when X is $sp^3$-hybridized C or Z represents O or an electronic lone-pair when X is N;
the dashed line represents a bond when X is $sp^2$-hybridized C or is absent when X is N;
m is an integer 1 or 2;
n is an integer 1-3;
provided that
when n in Formula 1 is 2, $R^1$ is $SO_2CH_3$ and $R^2$ is H $R^3$ does not represent n-propyl.

A specific embodiment of the compounds according to the invention is set forth in depending claim 2.

According to another aspect the present invention relates to a pharmaceutical preparation comprising as an active ingredient a compound according to the invention or a pharmaceutically acceptable salt thereof.

According to a further aspect the present invention relates to the use of a compound according to the invention or a pharmaceutically acceptable salt thereof for the manufacture of a pharmaceutical composition for the treatment of a disorder in the central nervous system.

According to a still further aspect, the present invention relates to a method for the treatment of a disorder in the central nervous system of a patient wherein a pharmaceutically active amount of a compound according to the invention or a pharmaceutically acceptable salt thereof is administered to said patient.

The compounds according to this invention possess, directly and/or indirectly, dopamine stabilizing/modulating properties and are useful in treating numerous central nervous system disorders including both psychiatric and neurological symptoms. Diseases in which compounds with stabilizing/modulating effects on dopaminergic systems may be beneficial are in disorders related to ageing, for preventing bradykinesia and depression and for the improvement of mental functions. They may also be used to ameliorate symptoms of mood disorders. They may be used in obesitas as an anorectic agent and in other eating disorders. They may be used to improve cognitive functions and related emotional disturbances in neurodegenerative disorders as well as after brain damage induced by vascular or traumatic insults. Likewise, cognitive and motor dysfunctions associated with developmental disorders appearing in infancy, childhood, or adolescence may improve. They can be used to improve all symptoms of schizophrenia and schizophreniform disorders, to improve ongoing symptoms as well as to prevent the occurrence of new psychotic episodes. Other psychotic disorders not characterized as schizophrenia, schizoaffective syndromes as well as psychotic symptoms, delusions and hallucinations induced by other drugs may also improve. Disruptive behavior disorders such as attention deficit hyperactivity disorder (ADHD), conduct disorder and oppositional defiant disorder may also improve. They can also be used in tic disorders such as Gilles de la Tourette's syndrome and other tic disorders. Also, speech disorders such as stuttering may improve. They may also be for regulating pathological disorders of food, coffee, tea, tobacco, alcohol and addictive drug intake and also to improve mental disorders associated with psychoactive substance overuse (including alcohol) including hallucinations, withdrawal symptoms, delusions, mood disorders, sexual and cognitive disturbances.

Anxiety disorders, obsessive-compulsive disorder and other impulse control disorders, post traumatic stress syndrome, personality disorders, and conversion hysteria may also be treated with the compounds in the invention. Other indications include-sleep disorders, "jetlag" and disorders of sexual functions.

Neurological indications include the treatment of Huntington's disease, movement disorders such as dyskinesias including other choreas as well as primary, secondary and paroxysmal dystonias, tardive movement disorders such as tardive dyskinesia and tardive dystonia as well as other drug induced movement disorders. Restless legs, periodic leg movements and narcolepsy may also be treated with compounds included in the invention. They may also improve mental and motor function in Parkinson's disease, and in related parkinsonian syndromes such as multiple system atrophies, progressive supranuclear palsy, diffuse Lewy body disorder and vascular parkinsonism. They may also be used to ameliorate tremor of different origins. The compounds in the invention can also be used for the treatment of vascular headaches such as migraine and cluster headache, both as acute and prophylactic treatment. They may improve rehabilitation following vascular or traumatic brain injury. Moreover, they may be used to relieve pain in conditions characterized by increased muscle tone.

The compounds according to the invention are especially suitable for treatment of disorders in the central nervous system, and particularly for treatment of dopamine mediated disorders. They may, e.g. used to ameliorate symptoms of mood disorders, in obesitas as an anorectic agent and in other eating disorders, to improve cognitive functions and related emotional disturbances, to improve cognitive and motor dysfunctions associated with developmental disorders, to improve all symptoms of psychosis, including schizophrenia and schizophreniform disorders, to improve ongoing symptoms as well as to prevent the occurrence of new psychotic episodes, to regulate pathological disorders due to intake of food, coffee, tea, tobacco, alcohol and addictive drugs etc.

The compounds according to the invention can thus be used to treat symptoms in e.g.: schizophrenia and other psychotic disorders, such as catatonic disorganized, paranoid, residual, or differentiated schizophrenia; schizophreniform disorder; schizoaffective disorder; delusional disorder; brief psychotic disorder; shared psychotic disorder; psychotic disorder due to a general medical condition with delusions and/or hallucinations; mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance induced mood disorder; anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, posttraumatic stress disorder, specific phobia, social phobia, and substance-induced anxiety disorder; eating disorders, such as anorexia nervosa, bulimia nervosa, and obesitas; sleep disorders, such as dyssomnias, e.g., breathing-related sleep disorder, circadian rhythm sleep disorder, hypersomnia, insomnia, narcolepsy, and "jet lag"; impulse-control disorders not elsewhere classified, such as intermittent explosive disorder, kleptomania, pathological gambling, pyromania, and trichotillomania; personality disorders, such as paranoid, schizoid or schizotypal disorder; antisocial, borderline, histrionic, and narcissistic disorder; and avoidant, dependent, obsessive-compulsive disorder; medication-induced movement disorders, such as neuroleptic induced parkinsonism, neuroleptic malignant syndrome, neuroleptic induced acute and tardive dystonia, neuroleptic induced akathisia, neuroleptic induced tardive dyskinesia, medication induced tremor, and medication induced dyskinesias; substance-related disorders, such as abuse, dependence, anxiety disorder, intoxication, intoxication delirium, psychotic disorder, psychotic disorder with delusions, mood disorder, persisting amnestic disorder, persisting dementia, persisting perception disorder, sexual dysfunction, sleep disorder, withdrawal, and withdrawal delirium due to use ore misuse of alcohol, amphetamine (or amphetamine-like substances), caffeine, cannabis, cocaine, hallucinogens, inhalants, nicotine, opioids, phencyclidine (or phencyclidine-like substances), sedative substances, hypnotic substances, and/or anxiolytic substances; disorders usually first diagnosed in infancy, childhood, or adolescence, such as mental retardation; learning disorders; motor skills disorders, e.g. developmental coordination disorder; communication disorders, e.g. expressive language disorder, phonological disorder, receptive-expressive language disorder and stuttering; pervasive developmental disorders, e.g. Asperger's disorder, autistic disorder, childhood disintegrative disorder, and Rett's disorder; attention-deficit and disruptive behavior disorders, e.g. attention-deficit/hyperactivity disorder, conduct disorder, and oppositional defiant disorder; feeding and eating disorders of infancy or early childhood, e.g. feeding disorder of infancy or early childhood, pica, rumination disorder; tic disorders, e.g. chronic motor or vocal tic disorder, and Tourette's disorder; other disorders of infancy, childhood, or adolescence, e.g. selective mutism, and stereotypic movement disorder; delirium, dementia, amnestic and other cognitive disorders, such as Alzheimer's, Creutzfeldt-Jakob disease, dead trauma, Huntington's disease, HIV disease, Pick's disease, and diffuse Lewy body dementia; conversion hysteria; conditions connected to normal ageing such as disturbances in motor functions and mental functions; Parkinson's Disease and related disorders, such as multiple system atrophies, e.g. striatonigral degeneration, olivopontocerebellar atrophy, and shydrager syndrome; progressive supranuclear palsy; corticobasal degeneration; and vascular parkinsonism; tremors, such as essential, orthostatic, rest, cerebellar, and secondary tremor headaches, such as migraine, cluster headache, tension type headache, and paroxysmal headache; movement disorders, such as dyskinesias, e.g. in general medicine condition, secondary to trauma or vascular insult, hemiballism, athetosis, Sydenham's chorea, and paroxysmal; dystonias; Ekbom's syndrome (restless legs); Wilson's Disease; Hallerworden-Spatz disease; rehabilitation medicine, e.g. to improve rehabilitation after vascular or traumatic brain injury; pain in conditions characterized by increased muscular tone, such as fibromyalgia, myofascial syndrome, dystonia, and parkinsonism; as well as conditions related to the above that fall within the larger categories but does not meet the criteria of any specific disorder within those categories.

The derivatives of this invention includes the pharmaceutically acceptable acid addition salts thereof. By the term "pharmaceutically acceptable acid addition salt" is meant any non-toxic pharmaceutically suitable salt of a compound described above which has the desired pharmacological properties in mammals. Preparation of such salts is well known to those skilled in pharmaceutical science. Pharmaceutically acceptable acid addition salts of the above compounds include the hydrochloride, hydrobromide, hydroiodide, sulfate, bisulfate, nitrate, citrate, tartrate, bitartrate, lactate, phosphate, malate, maleate, fumarate, succinate, acetate and pamoate.

Also provided is a method for converting a suitable precursor to its N-oxide drug/prodrug, which comprises reacting the precursor with a suitable oxidizing agent in a suitable solvent.
Chemistry The syntheses of the intermediates (the compounds of Formulas 1 and 2 less the N-oxides) used as starting materials for N-oxidation have been described in the patent applications WO 92/18475 and US 2003/0004169 A1.

There are a number of oxidizing agents that may be used to convert tertiary amines to tertiary amine N-oxides. Metachloroperbenzoic acid is convenient because it generally reacts rapidly to produce the N-oxide. However, other organic peracids may be used, such as performic acid, peracetic acid, perbenzoic acid, pertrifluoroacetic acid, permaleic acid, and perphthalic acid. Alternatively, the oxidizing agent may be produced in situ by dissolving the tertiary amine in an acid such as formic acid, acetic acid, or trifluoroacetic acid, and adding aqueous hydrogen peroxide of 3%-50% concentration, preferably of 30% to 50% concentration. An aprotic solvent such as methylene chloride, chloroform, or 1,2-dichloroethane, or a protic solvent such as CF3COOH, methanol, ethanol, propanol, or tertiary butanol, may be used as the reaction medium, or if the oxidizing agent is generated in situ, the acid may optionally be used as the reaction medium.

Instead of using an organic peracid as described above, one may use a peroxide such as hydrogen peroxide. Aqueous hydrogen peroxide may be used alone in concentrations of 3% to 50%, or it may be used in a solvent such as those listed above. Other oxidizing agents which may be used include ozone, tertiary butyl hydroperoxide, and cumene hydroperoxide.

In general, the oxidizing agents are employed at temperatures between 0° C. and the boiling point of the solvent, more specifically between room temperature and the boiling point of the solvent, and for times between several minutes and three days, more specifically between one hour and 24 hours. The peroxide may be used in a ratio of one equivalent of peroxide to one equivalent of the amine, or an excess of peroxide may be used, such as between 10% and 100% excess or more. In order to prepare the di-N-oxides, at least two equivalents are needed. If, at the end of the reaction, excess peroxide is present (most easily detected with starch-iodide paper) it may be destroyed by adding an inorganic reducing agent such as sodium bisulfite or sodium sulfite, a metal catalyst such as 5% platinum or palladium on carbon or alumina, or an organic reducing agent such as dimethyl sulfide or $CS_2$.

Other oxidizing agents that may be used for the preparation of tertiary amine oxides are ozone in a solvent such as chloroform, methylene chloride, a Freon, or methanol; ozone adsorbed on silica gel; and hydroperoxides such as tertiary butyl hydroperoxide, optionally in the presence of a catalyst such as a vanadium compound.

When cost is important, for example in preparation on an industrial scale, the preferred reagent is 30%-50% aqueous hydrogen peroxide in tertiary butanol as solvent.

Methods for preparation of a number of compounds of this invention are demonstrated in the following Examples, which are not intended to limit the scope of the present invention.

EXPERIMENTAL SECTION

General

IR spectra were obtained on an ATI-Mattson Genesis Series FTIR spectrometer. NMR spectra were obtained on a Varian Gemini 300 spectrometer. Chemical shifts are reported in δ value (ppm). Mass spectra (ES) were recorded on a PE SCIEX API 3000 LCMS/MS System mass spectrometer. Mass spectra (EI) were recorded on a Shimadzu GC-17A GCMS-QP50000 CP-Sil 5-CB Low-bleed/MS 15 m/0.25 mm ID/0.10 µm GC-MS system, auto sampler/injector AOS-20. Gas chromatography was performed on a HP 5890 Series II CP-Sil 5-CB Chrompack 15 m/0.25 mm ID/0.10 µm gas chromatograph. Catalytic reduction with hydrogen gas pressure was performed on a Gerhardt Parr apparatus. Optical rotation was performed on a Perkin-Elmer 241 polarimeter. HPLC was performed on a Waters Chiral PAK AD column.

4-(3-Methylsulfanyl-phenyl)-1-propyl-piperidin-4-ol (1)

Chemical Formula: $C_{15}H_{23}NOS$
Exact Mass: 265.15
Molecular Weight: 264.41
m/z: 265.15 (100.0%), 266.15 (17.4%), 267.15 (4.9%), 267.16 (1.3%)
Elemental Analysis: C, 67.88; H, 8.73; N, 5.28; O, 6.03; S, 12.08

3-Bromothioanisole (960 mg, 4.73 mmol) was dissolved in 10 mL of diethyl ether dried on Na. 1-Propyl-4-piperidone was dissolved in 8 mL of dry diethyl ether. Approximately 10% of the solution of 3-bromothioanisole in dry diethyl ether was added to magnesium (344 mg, 14.15 mmol) and a few iodine crystals in a dried 250 mL three-necked flask in a nitrogen atmosphere. When the brown mixture turned colourless, the remaining solution of 3-bromothioanisole in dry diethyl ether was added drop wise, while refluxing on a hot water bath in a nitrogen atmosphere. When all the solution was added, the reaction mixture was left to reflux for twenty minutes. Then, 10 mL of dry diethyl ether was added because of evaporation. It was left to reflux for 30 minutes. The reaction mixture turned yellow and then green. Gas forming was noticed even before refluxing. Then the reaction mixture was left to cool to room temperature. The solution of 1-propyl-4-piperidone in dry diethyl ether was added drop wise to the reaction mixture. The reaction mixture then consisted of a dark oil, white precipitation and some clear solution. The reaction mixture was worked up with saturated $NH_4Cl$ solution (30 mL). The organic layer was separated. The aqueous layer was extracted twice with diethyl ether. The organic layers were collected and washed with brine and dried on MgSO$_4$ during the night. The solution was filtered and the solvent evaporated in vacuo on a rotavapor. No further purification. Yield: 460 mg (56%). IR (KBr): 3113, 2956, 2917, 2828, 2772, 2365, 1583, 1444, 1375, 1148, 1104, 1044, 780, 696 cm$^{-1}$; $^1$H-NMR (CDCl$_3$, 300 MHz): δ 7.280 (d), 7.159 (m), 2.820 (d), 2.484 (s), 2.433 (t), 2.195 (t), 1.761 (d), 1.588 (t), 0.924 (t) ppm; $^{13}$C-NMR (CDCl$_3$, 300 MHz): δ 127.291, 123.521, 121.359, 119.865, 69.826, 59.311, 47.947, 36.864, 18.573, 14.310, 10.524 ppm; GCMS (EI): m/z 265 (M+), 236 (M−29), 218, 206, 118; GC (100-320° C., 15° C./min): 7.6 min.

4-(3-Methylsulfanyl-phenyl)-1-propyl-1,2,3,6-tetrahydropyridine (2)

Chemical Formula: C$_{15}$H$_{21}$NS
Exact Mass: 247.14
Molecular Weight: 247.4
m/z: 247.14 (100.0%), 248.14 (17.4%), 249.14 (4.7%), 249.15 (1.3%)
Elemental Analysis: C, 72.82; H, 8.56; N, 5.66; S, 12.96

4-(3-Methylsulfanyl-phenyl)-1-propyl-piperidin-4-ol (1) (100 mg, 0.38 mmol) was dissolved in 2 mL of trifluoroacetic acid (TFA) in a 50 mL flask while stirring in a nitrogen atmosphere. The reaction mixture was heated to reflux on an isomantle. After 15 minutes the reaction mixture was cooled to room temperature. The TFA was removed by distillation under reduced pressure. The remaining brown oil was dissolved in diethyl ether, washed 3 times with water and once with brine. The aqueous layers and brine layer were collected, basified with Na$_2$CO$_3$ and extracted with diethyl ether twice. The organic layers were collected, dried on MgSO$_4$, filtered and the solvent was evaporated under reduced pressure using a rotavapor. Yield: 103 mg (111%). GCMS (EI): m/z 247 (M+), 218 (M−29); GC (100-320° C., 15° C./min): 7.6 min.

4-(3-Methylsulfanyl-phenyl)-1-propyl-piperidine (3)

Chemical Formula: C$_{15}$H$_{23}$NS
Exact Mass: 249.16
Molecular Weight: 249.41
m/z: 249.16 (100.0%), 250.16 (16.5%), 251.15 (4.5%), 251.16 (1.5%), 250.15 (1.2%)
Elemental Analysis: C, 72.23; H, 9.29; N, 5.62; S, 12.86

4-(3-Methylsulfanyl-phenyl)-1-propyl-1,2,3,6-tetrahydropyridine (2) (290 mg, 1.17 mmol) was brought in a Parr-flask with 10 mL of ethanol (100%) in a nitrogen atmosphere. 100 mg of Pd/C and 0.5 mL of HCl (37%) were added. The flask was attached to a Parr reduction apparatus and H$_2$ gas was added to a pressure of 3 Bar. It was left shaking for 1 h. Then, the mixture was filtered over celite, put back in the flask and another 100 mg of Pd/C and 1 ml of HCl (37%) was added before attaching the flask to the Parr apparatus again and starting another session of 75 min this time. This procedure was repeated another 3 times, with session durations of 105 min, 1 night and 2 h. Eventually, the mixture was filtered, the solvent evaporated in vacuo on a rotavapor. 10 mL of NaHCO$_3$ 10% was added (pH 8). Then 30 mL of water and 40 mL of diethyl ether were added and shaken. The aqueous layer was extracted three times with diethyl ether. The combined organic layers were washed with brine, dried on MgSO$_4$, filtered and the solvent was evaporated on a rotavapor. The slightly yellow oil was taken up in CH$_2$Cl$_2$ and purified by gradient column chromatography (Al$_2$O$_3$, CH$_2$Cl$_2$, CH$_2$Cl$_2$:MeOH 10:1). Fractions 9-20 contained the desired product. The fractions were collected and the solvent was evaporated in under reduced pressure. Yield: 335 mg (115%). The reaction was followed on thin layer chromatography (SiO$_2$ flushed with NH$_3$, CH$_2$Cl$_2$:MeOH 20:1 and Al$_2$O$_3$, CH$_2$CL$_2$:MeOH 40:1). $^1$H-NMR (CDCl$_3$, 300 MHz): δ 7.2 (m), 3.1 (t), 2.5 (s), 2.4 (m), 2.0 (m), 1.8 (m), 1.6 (m), 1.2 (m), 0.9 (m) ppm; $^{13}$C-NMR (CDCl$_3$, 300 MHz): δ 145.673, 136.767, 127.345, 126.882, 126.722, 125.372, 124.576, 123.650, 123.430, 122.793, 122.216, 120.479, 59.631, 52.841, 41.333, 31.888, 26.630, 18.680, 14.287, 10.577 ppm; GCMS (EI): m/z 249 (M+), 220 (M−29); GC (100-320° C., 10° C./min): 4.7, 9.9 min.

4-(3-Methanesulfonyl-phenyl)-1-propyl-piperidine-1-oxide (4, ACR16-N-oxide)

Chemical Formula: C$_{15}$H$_{23}$NO$_3$S
Exact Mass: 297.14
Molecular Weight: 297.41
m/z: 297.14 (100.0%), 298.14 (17.5%), 299.14 (5.3%), 299.15 (1.3%)
Elemental Analysis: C, 60.58; H, 7.79; N, 4.71; O, 16.14; S, 10.78

4-(3-Methylsulfanyl-phenyl)-1-propyl-piperidine (3) (240 mg, 0.96 mmol), 3-chloroperoxybenzoic acid (672 mg, 3.88 mmol) and 2 mL of TFA were added to 30 mL of CH$_2$Cl$_2$ while stirring and cooling on ice water. Stirring was continued for 1 h. The solvent was evaporated in vacuo on a rotavapor. The remaining oil was refrigerated when not used. The white solid was treated with a 10% NaHCO$_3$ solution and the mixture was extracted with CH$_2$Cl$_2$ three times. The organic layers were combined, dried on MgSO$_4$ and filtered. The solvent was evaporated in vacuo on a rotavapor. It was purified by gradient column chromatography (acidic Al$_2$O$_3$, CH$_2$Cl$_2$, CH$_2$Cl$_2$:MeOH 20:1). Fractions 19-36 contained the desired product, though not pure. Fractions 19-36 were pure, fractions 14-18 were purified again by gradient column chromatography (Al$_2$O$_3$, CH$_2$Cl$_2$, CH$_2$Cl$_2$:MeOH 20:1). Fractions 10-30 contained the desired product though not pure. Fractions 10-12 were pure, fractions 13-30 were purified again by gradient column chromatography (Al$_2$O$_3$, CH$_2$Cl$_2$, CH$_2$Cl$_2$:MeOH 40:1). Fractions 11 and 12 contained the pure desired product. Yield: 109 mg (39%). $^1$H-NMR (CDCl$_3$, 300 MHz): δ 7.841 (m), 7.777 (m), 3.4287 (s), 3.043 (s), 2.731 (m), 1.971 (m), 1.800 (d), 0.999 (t); $^{13}$C-NMR (CDCl$_3$, 300 MHz): δ 144.543, 139.300, 130.546, 128.300, 124.431, 124.189, 76.168, 74.893, 72.261, 62.733, 62.733, 42.933, 39.170, 25.985, 14.355, 9.705; MS (ES): m/z 298 (M+H), 282 (M−O); GCMS (EI): m/z 281 (M−O), 268 (M−O−29); GC (100-320° C., 15° C./min): 8.6 min.

4-(3-Methanesulfonyl-phenyl)-1-propyl-piperidin-4-ol-1-oxide (5)

Chemical Formula: C$_{15}$H$_{23}$NO$_4$S
Exact Mass: 313.13
Molecular Weight: 313.41
m/z: 313.13 (100.0%), 314.14 (16.6%), 315.13 (4.5%), 315.14 (2.3%), 314.13 (1.2%)
Elemental Analysis: C, 57.48; H, 7.40; N, 4.47; O, 20.42; S, 10.23

Five equivalents of 3-chloroperoxybenzoic acid 70-75% (2115 mg, 9.45 mmol) were dissolved in CH$_2$Cl$_2$ (15 mL). 4-(3-Methylsulfanyl-phenyl)-1-propyl-piperidin-4-ol (1) (507 mg, 1.89 mmol) was dissolved in CH$_2$Cl$_2$ (20 mL) in a 100 mL flask. 12 mL of the 3-chloroperoxybenzoic acid solution was added to the flask while stirring. The reaction mixture was left stirring for 2 h. Then, another 3 mL of the 3-chloroperoxybenzoic acid solution was added while stirring. After 2 h, the stirring was stopped and the reaction mixture was left standing at room temperature overnight. A few mL were taken from the solution. Crystallisation took place after evaporating some solvent on a rotavapor by adding some cold CH$_2$Cl$_2$. 5 mg of white crystals were collected after filtration, rinsing and drying in a desiccator. The remaining reaction mixture was purified by gradient column chromatography (Al$_2$O$_3$, CH$_2$Cl$_2$:MeOH 40:1, CH$_2$Cl$_2$:MeOH 20:1). This was done two more times with the fractions that contained the desired product. Fractions 19-23 of the third column contained the desired product, but not pure. Crystallisation was performed with EtOH and diethyl ether. The collected crystals were dissolved and the purity of this sample was checked on HPLC. The purity was estimated to be between 80 and 90%. Then ion-pairing agent 3,5-di-tert-Bu-2-OH-phenyl-sulphonic acid was added to the mixture of the raw product, water holding a pH of ca 1 and CH$_2$Cl$_2$ and extraction was performed. The organic layers were combined, dried on MgSO$_4$ and filtered. The solvent was evaporated on a rotavapor. The desired product in the remaining oil was purified by column chromatography (Al$_2$O$_3$, CH$_2$Cl$_2$:MeOH 20:1). Fractions 14-22 contained the desired product, which crystallised in the solution. The crystals were collected by centrifugation in diethyl ether. Yield: 104 mg (19%) (without ion-pairing agent). $^1$H-NMR (CDCl$_3$, 300 MHz): δ 8.3129 (t), 7.728 (m), 6.628 (m), 6.394 (d), 5.844 (m), 5.673 (m) ppm; $^{13}$C-NMR (CDCl$_3$, 300 MHz): δ 128.728, 127.559, 122.097, 71.739, 67.354, 58.751, 42.698, 39.239, 38.806, 37.972, 37.547, 31.485, 14.037, 9.614 ppm; MS (ES): m/z 314 (M+H); GCMS (EI): m/z 297 (M−O).

3-(3-Methoxy-phenyl)-1-benzylpiperidine (6)

3-Bromoanisole (14.824 g, 79.26 mmol) was dissolved in 160 mL of diethyl ether dried on Na. Approximately 10% of the solution of 3-bromoanisole in dry diethyl ether was added to magnesium (1.927 g, 79.27 mmol) and a few iodine crystals in a dried 500 mL three-necked flask in a nitrogen atmosphere while stirring. Almost instantly, H$_2$ gas was visible. The brown mixture turned colourless. The remaining solution of 3-bromoanisole in dry diethyl ether was added drop wise. Gas forming was noticed during and after this. After 1 h, a lot of white precipitate was noticed. 1-Benzyl-3-piperidone (5.000 g, 26.42 mmol) was dissolved in 120 mL of dry diethyl ether and added to the reaction mixture drop wise at 30° C. The fine white/yellow precipitate turned more coarse and brownish. Stirring was continued at room temperature for 1 h. Then the suspension was poured in a Erlenmeyer flask and 150 mL of saturated NH$_4$Cl solution was added. About 50 mL of ethylacetate was added to wash out the three-necked flask. The suspension was stirred for 5 min. The organic layer was separated and the aqueous layer was extracted three times with diethyl ether. The organic layers were collected, washed with brine and dried on NaSO$_4$ overnight. The solution was filtered and the solvent evaporated. The residue (about 12.000 g) was extracted with ether once, the solvent evaporated. Yield: 7.6 g (32%). GCMS (EI): m/z 297 (M+), 206 (M−91), 177, 147, 134; GC (100-320° C., 15° C./min): 9.1 min.

3-(3-Methoxy-phenyl)-1-benzyl-1,2,3,6-tetrahydro-pyridine (7)

3-Benzyl-1-(3-methoxy-phenyl)-cyclohexanol (8) (7.640 g, 25.72 mmol) was dissolved in 20 mL of TFA in a 50 mL flask while stirring in a nitrogen atmosphere. For 3 h the reaction mixture was stirred. Then the reaction mixture was heated to reflux overnight. Thereafter the reaction was stopped and the TFA was removed. The remaining oil was basified with a 50% diluted saturated NaHCO$_3$ solution and extracted with CH$_2$Cl$_2$ twice. The organic layers were collected, dried on Na$_2$SO$_4$ and the solvent was evaporated. The dark oil was purified by gradient column chromatography (SiO$_2$, CH$_2$Cl$_2$, CH$_2$Cl$_2$:MeOH 1:1). Fractions 23-27 contained the desired product. Yield: 4.9 g (64%). GC (100-320° C., 15° C.): 8.9, 9.4 min.

Resolution of 3-(3-Methoxy-phenyl)-1-benzylpiperidine (R- and S-8) 1-Benzyl-5-(3-methoxy-phenyl)-1,2,3,6-tetrahydropyridine (7)

(4580 mg, 16.42 mmol) was brought in a Parr-flask with 100 mL of ethanol and 300 mg of Pd/C in a nitrogen atmosphere. The flask was attached to a Parr reduction apparatus and left shaking for 1% h with a H$_2$ pressure of 3 Bar. The reaction mixture was then filtered and the solvent evaporated in vacuo on a rotavapor. Then (−)-dibenzoyl-L-tartaric acid monohydrate (5750 mg, 15.28 mmol) and 60 mL of methanol were added. The reaction mixture was refluxed while stirring for ½ h. Some methanol was evaporated by heating and a few mL of diethyl ether were added. The reaction mixture was left to cool and stand over 5 nights. White crystals appeared in an orange solution. The suspension was decanted. The crystals were stirred in cold methanol on ice. The suspension was filtered and dried. The remaining orange solution was crystallised once more using (+)-dibenzoyl-D-tartaric acid monohydrate (5370 mg, 14.99 mmol). The appearing white precipitant was treated in the same way as its enantiomer. Yield (+): 2.8 g (60%). Yield (−): 2.7 g (59%). α=−44; GCMS (EI): m/z 281 (M+) 204, 190, 161, 146, 134; GC (100-320° C., 15° C./min): 8.5 min.

S-3-(3-Methoxy-phenyl)-piperidine (S-9)

1-Benzyl-3-(3-methoxy-phenyl)-piperidine (S-8) (306 mg, 1.09 mmol) was added to Pd/C (250 mg), ammoniumformate (270 mg, 62.06 mmol) and 125 mL of methanol. The reaction mixture was brought to reflux while stirring in a nitrogen atmosphere for 1 h. Then the reaction mixture was left to cool to room temperature. The reaction mixture was filtered. To the filtrate some methanol was added and refluxed shortly. Again, this was filtered. Both methanol fractions were combined and the solvent was evaporated. Yield: 196 mg (94%). GCMS (EI): m/z 191 (M+), 162 (M−29); GC (100-320° C., 15° C./min): 4.3 min.

S-3-(3-Methoxy-phenyl)-1-propyl-piperidine (S-10)

3-(3-Methoxy-phenyl)-piperidine (S-9) (180 mg, 0.94 mmol) and (n)-propyliodide (240 mg, 1.41 mmol) and caesiumcarbonate (614 mg, 1.88 mmol) were added to 50 mL of acetonitrile in a nitrogen atmosphere while stirring. It was left to stir overnight. TLC showed some starting material still present and cesiumcarbonate (305 mg, 0.94 mmol) was added in a few mL of acetonitrile. Also (n)-propyliodide (170 mg, 1.00 mmol) was added in a few mL of acetonitrile. The reaction mixture was refluxed for 4 h. The reaction mixture was left to cool to room temperature and was slightly yellow. The reaction mixture was filtered and the solvent was evaporated. Then it was dissolved in $CH_2Cl_2$. Some cesiumcarbonate was still present. The reactions mixture was washed three times with water and once with brine, was then dried on $MgSO_4$, filtered and the solvent was then evaporated. The remaining oil was taken up in $CH_2Cl_2$ and purified by column chromatography ($SiO_2$, $CH_2Cl_2$:MeOH 20:1). Fractions 18-42 contained the desired product. Yield: 121 mg (55%). $^1$H-NMR ($CDCl_3$, 300 MHz): δ 7.214 (t), 6.776 (t), 5.289 (s), 3.793 (s), 3.019 (s), 2.847 (t), 2.344 (t), 1.976 (t), 1.772 (s), 1.531 (t), 0.890 (t) ppm; $^{13}$C-NMR ($CDCl_3$, 300 MHz): δ 144.89, 127.787, 118.114, 111.757, 109.853, 59.616, 53.630, 52.363, 41.333, 30.029, 24.112, 18.414, 10.479 ppm; GCMS (EI): m/z 233 (M+) 204 (M−29), 161, 135, 121; GC (100-320° C., 15° C./min): 5.3 min.

S-3-(1-Propyl-piperidin-3-yl)-phenol (S-3-PPP; S-11)

S-3-(3-Methoxy-phenyl)-1-propyl-piperidine (S-10) (130 mg, 0.56 mmol) was added to 10 mL of HBr (48%) while stirring in a nitrogen atmosphere and refluxed for ½ h. The solvent was distilled off the reaction mixture in vacuo, leaving it dry. Three times ethanol (100%) was added and was distilled off the reaction mixture in vacuo, leaving it dry again. Then a few mL of a 10% $NaHCO_3$ solution was added. The mixture was extracted three times with $CH_2Cl_2$. The organic layers were combined, washed once with brine, dried on $MgSO_4$ and filtered. The solvent was evaporated. Yield: 125 mg (102%). GCMS (EI): m/z 219 (M+), 190 (M−29); GC (100-320° C., 15° C./min): 5.7 min.

S-3-Trifluoro-methanesulfonyloxy-(1-n-propyl-phenyl)piperidine (S-12)

S-3-(3-Hydroxyphenyl)-N-n-propylpiperidine (S-3-PPP; S-11) (102.1 mg, 0.40 mmol) and N-phenyltrifluoromethanesulfonimide (195 mg, 0.55 mmol) were dissolved in dry $CH_2Cl_2$ (over $Al_2O_3$) (40 mL). The mixture was cooled to −60° C. Triethylamine (500 μL, 3.60 mmol) was added drop wise in a period of 45 min. The temperature was kept at −50° C. for another 10 min. Then, the reaction mixture was slowly brought to room temperature (11° C.). The reaction mixture was left standing overnight. Then, N-phenyltrifluor-methanesulfonimide (80 mg, 0.22 mmol) was added at −60° C. After that, the temperature was slowly brought to 10° C. The reaction mixture was left standing overnight once more. Then, the reaction mixture was extracted three times with water (10 mL) and finally once with brine. The organic layers were combined, dried over $MgSO_4$ and filtered. The solvent was evaporated. The remaining substance was purified by column chromatography ($SiO_2$, $CH_2Cl_2$:MeOH 20:1) Yield: 280 mg (96%). $^1$H-NMR ($CDCl_3$, 300 MHz): δ 7.382 (d), 7.343 (d), 7.305 (d), 7.255 (m), 7.216 (t), 7.112 (m), 7.073 (m), 2.940 (m), 2.810 (m), 2.349 (s), 2.311 (m), 2.271 (s), 2.013 (d), 1.958 (d), 1.904 (d), 1.749 (m), 1.529 (m), 0.874 (t) ppm; $^{13}$C-NMR ($CDCl_3$, 300 MHz): δ 79.988, 78.105, 60.231, 57.667, 52.137, 50.248, 49.254, 45.756, 7.877, 7.240, 6.603, −8.729, −9.002, −27.255, −38.332, −44.393, −49.772, −57.806 ppm; MS (ES): m/z 352 (M+H).

S-Trifluoromethanesulfonic acid 3-(1-propyl-piperidin-3-yl)-phenyl ester-1-oxide (S-3-PPP-OTf-N-ox; S-13)

S-Trifluoro-methanesulfonic acid 3-(1-propyl-piperidin-3-yl)-phenyl ester, which has been described by Sonesson et al. as compound 6 in Journal of Medicinal Chemistry, 1994, Vol. 37, No. 17, (Mw 351, 100 mg, 285 μmol) was dissolved in about 5 mL methylene chloride. To this solution was added (at room temperature) m-chloroperbenzoic acid (MCPBA, Mw 173, 200 mg, 1160 μmol). A TLC (alumina eluting with methylene chloride/methanol 20/1) was run after about one hour and showed no starting material and a new spot, about half way on the plate. The same eluent was used when chromatography in a Pasteur pipette (alumina). About 1 mL fractions were collected and the product was isolated and the solvents were removed by evaporation, leaving a solid (50 mg), which was identified by API MS (M+1=368).

4-(3-Methanesulfonyl-phenyl)-1-propyl-1,2,3,6-tetrahydro-pyridine-N-oxide (14, ACR16-ene-N-oxide)

A small amount (about 50 mg) of the Grignard reagent of 3-methylsulfanylbromobenzene was generated and was allowed to react with n-propyl-3-piperidone, forming 4-(3-methylsulfanyl-phenyl)-1-propyl-piperidin-4-ol, which was dehydrated in refluxing TFA and thereafter oxidized with mCPBA. The reaction mixture was applied to the top of a Pasteur pipette filled with neutral Al2O3, eluting with about 10 mL CH2Cl2, 10 mL $CH_2Cl_2$:MeOH (40:1) and finally 10 mLCH2Cl2:MeOH (20:1). The fractions containing nearly pure (>90%) 4-(3-methanesulfonyl-phenyl)-1-propyl-1,2,3, 6-tetrahydro-pyridine-N-oxide (14, MS API direct inlet showed M+1=296.

Pharmacology

Microdialysis in Rat Striatum Standard microdialysis experiments were performed on-line in freely moving rats. The striatum was perfused with a Ringer solution and dopamine, DOPAC and 5-HIAA were quantified by HPLC with electrochemical detection.

Surprisingly, a pronounced pharmacological effect with a very long duration of action for e.g. the N-oxide of compound 3-OTf-PPP (see graph below) was registered. In addition, and also surprisingly, it was found that infusion of some of the N-oxide compounds displayed an altered biochemical response, as compared to controls, when infused at different concentrations within the Ringer solution into the striatum of the microdialysis rats. This shows that these N-oxides are not inactive per se at the receptor or at another level of the dopamine neurons. This activity is different from that displayed by the corresponding basic amine analogs and may give an added value to the N-oxide prodrugs, which is beneficial to the therapeutic potential of these new compounds.

4-(3-Methanesulfonyl-phenyl)-1-propyl-piperidine-1-oxide (4, ACR16-N-oxide)

First, 50 µmol/kg was administered per os, resulting in a considerable rise in dopamine (DA) level after about 45 minutes and a slight rise in 3,4-dihydroxyphenylacetic acid (DOPAC) level. 180 minutes (3 hours) 100 µmol/kg ACR16 N-oxide was administered per os. Almost immediately, the level of dopamine rises to a peak after 240 minutes (4 hours) at a maximum height of more than 250% of controls. The 3,4-dihydroxyphenylacetic acid (DOPAC) level also goes up.

S-3-Trifluoro-methanesulfonyloxy-(1-n-propyl-phenylpiperidine (S-3-PPP Triflate; S-12)

The results of testing the reference compound (−)-3-PPP triflate are given here: 100 µmol/kg was (−)-3-PPP triflate administered per os. Almost immediately, a rise in dopamine (DA) and 3,4-dihydroxyphenylacetic acid (DOPAC) level is observed to a maximum of about 175% after about 150 minutes (2.5 hours). The level of 5-hydroxyindolacetic acid (HIAA) around 100%. After about 195 minutes (3.25 hours), both levels of dopamine and 3,4-dihydroxyphenylacetic acid (DOPAC) decrease.

After about 240 minutes (4 hours), a sudden increase of both levels are observed again, with a remarkable rise of the dopamine level to 350% of controls.

S-3-Trifluoro-methanesulfonyloxy-(1-n-propyl-phenylpiperidine N-oxide (S-3-PPP triflate-N-oxide; S-13)

The results of testing S-3-PPP triflate-N-oxide are given here: 100 µmol/kg was S-3-PPP triflate-N-oxide administered per os. Almost immediately, a rise in dopamine (DA) and 3,4-dihydroxyphenyl-acetic acid (DOPAC) level is observed to a maximum of about 230% and 150%, respectively after about 120 minutes (2 hours). These levels were constant over the whole experiment (6 h). The level of 5-hydroxyindolacetic acid (HIAA) was around 100%.

Microdialysis with compound 4-(3-methanesulfonylphenyl)-1-propyl-1,2,3,6-tetrahydro-pyridine-N-oxide (compound 14)

The result after oral administration of 9.2 mg (9200/295 µmol=31 µmol) of ACR16-ene-N-ox dissolved in 10 µL HOAc and 1 mL water in a rat (340 g=>31/0.340=91 µmol/kg) were: an increase in DA and DOPAC release to about 300% of controls. The duration of these effects was >4 h.

Pharmacokinetics

In order to be able to collect drug samples from the striatum of this particular rat, it also received a "hollow fibre" membrane microdialysis probe inserted into the striatum "on the other side", as compared to the Hospal membrane probe (see above).

On the day after the operation, the rat (see PHARMACOLOGY above) received compound S-3-OTf-3-PPP-N-ox (13; 100 µmol/kg, p.o.) and drug and precursor concentrations (expressed in counts/s (cps)) were monitored every 1 h from the other striatum. 3-OTf-3-PPP-N-ox was measured at Rt=11.68 min with a +MRM of 368/235. Precursor 3-OTf-3-PPP was measured at Rt=11.50 min with a +MRM of 352/219.

Figure 1:
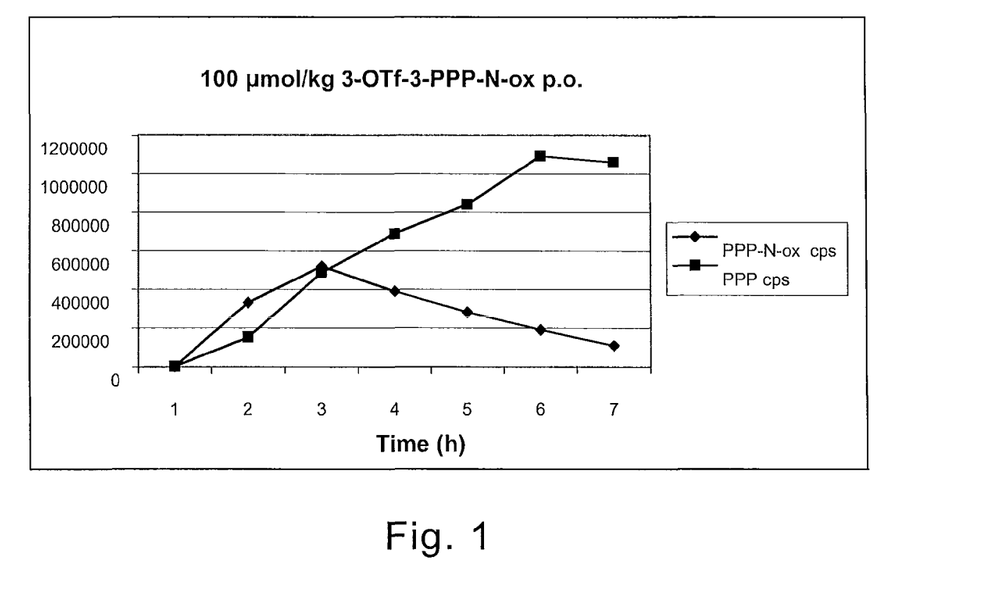
FIGS. 1 and 2 shows the drug and precursor concentration (expressed in counts/s) over time.
Figure 2:
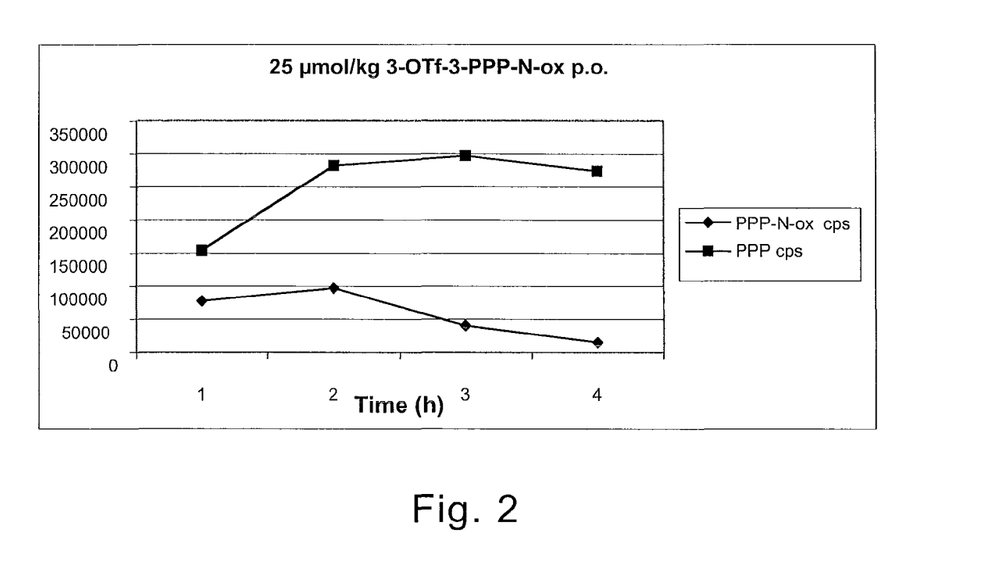

Analysis was performed with a HPLC/MS/MS gradient (CH3CN/water from 15% to 95% for CH3CN for a total cycle of 30 min) system and gave the following result, which surprisingly indicates a continuous rise of the striatal concentration of compound 12 between 0 h and 6 h (see FIGS. 1 and 2).

The invention claimed is:

1. A pharmaceutical composition comprising a pharmaceutically acceptable carrier or diluent, together with an N-oxide of formula (2)

(2)

wherein
$R^1$ is $SO_2CH_3$;
$R^2$ is H, F, Cl or $CH_3$;
$R^3$ is n-propyl or ethyl;
X is C;
Y is O; and
Z is H,
or a pharmaceutically acceptable salt of the N-oxide.

2. The pharmaceutical composition according to claim 1, wherein the N-oxide is 4-(3-Methanesulfonyl-phenyl)-1-propyl-piperidine-1-oxide, or a pharmaceutically acceptable salt thereof.

* * * * *